(12) United States Patent
Patnaikuni et al.

(10) Patent No.: US 12,097,374 B2
(45) Date of Patent: Sep. 24, 2024

(54) AUDIO-VISUAL INTERACTION WITH IMPLANTED DEVICES

(71) Applicant: International Business Machines Corporation, Armonk, NY (US)

(72) Inventors: Subha Kiran Patnaikuni, Visakhapatnam (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 253 days.

(21) Appl. No.: 17/027,957

(22) Filed: Sep. 22, 2020

(65) Prior Publication Data

US 2022/0088397 A1    Mar. 24, 2022

(51) Int. Cl.
| | | |
|---|---|---|
| A61N 1/372 | (2006.01) | |
| A61N 1/08 | (2006.01) | |
| G06F 3/01 | (2006.01) | |
| G06F 3/16 | (2006.01) | |
| G06T 15/00 | (2011.01) | |

(52) U.S. Cl.
CPC ........... *A61N 1/37217* (2013.01); *A61N 1/08* (2013.01); *G06F 3/011* (2013.01); *G06F 3/167* (2013.01); *G06T 15/005* (2013.01)

(58) Field of Classification Search
CPC ....... A61N 1/08; A61N 1/37217; G06F 3/011; G06F 3/167; G06T 15/005
USPC .......................................................... 607/60
See application file for complete search history.

(56) References Cited

U.S. PATENT DOCUMENTS

| | | | |
|---|---|---|---|
| 6,453,201 B1 | 9/2002 | Daum | |
| 6,824,512 B2 | 11/2004 | Warkentin | |
| 8,002,701 B2 * | 8/2011 | John | G16H 40/67 |
| | | | 128/903 |
| 8,183,998 B2 | 5/2012 | Rao | |
| 9,192,773 B2 * | 11/2015 | Forsell | A61M 5/142 |
| 2010/0280336 A1 | 11/2010 | Giftakis | |

(Continued)

FOREIGN PATENT DOCUMENTS

WO    2017090041 A1    6/2017

OTHER PUBLICATIONS

"Method and system for digital twin-based realtime and predicted health condition visualization with augmented reality glass", IP.com No. IPCOM000262365D IP.com Electronic Publication Date: May 23, 2020 5 pps., <https://priorart.ip.com/IPCOM/000262365>.

(Continued)

*Primary Examiner* — Carl H Layno
*Assistant Examiner* — Manolis Pahakis
(74) *Attorney, Agent, or Firm* — Yee & Associates, P.C.

(57) ABSTRACT

Aspects of the present invention disclose a method for audio-visual interaction of a user and implant device to resolve a voice command of the user. The method includes one or more processors determining a health-related issue of a user that corresponds to a voice command of the user. The method further includes identifying an implanted device of the user that relates to the health-related issue. The method further includes collecting sensor data of the implanted device, wherein the sensor data includes one or more conditions of the implanted device and operating environment of the implanted device in the body of the user. The method further includes generating an audio-visual response corresponding to the health-related issue of the user.

20 Claims, 3 Drawing Sheets

(56) References Cited

U.S. PATENT DOCUMENTS

| | | | |
|---|---|---|---|
| 2015/0164376 A1 | 6/2015 | Huang | |
| 2015/0290454 A1* | 10/2015 | Tyler | G06F 3/012 |
| | | | 607/134 |
| 2016/0302692 A1* | 10/2016 | Demmer | A61B 5/6898 |
| 2017/0017373 A1 | 1/2017 | Yim | |
| 2017/0258526 A1* | 9/2017 | Lang | A61B 17/1775 |
| 2017/0323481 A1* | 11/2017 | Tran | H04N 5/23219 |
| 2018/0133507 A1* | 5/2018 | Malchano | A61N 1/36036 |
| 2019/0001135 A1* | 1/2019 | Yoo | A61N 1/36132 |
| 2019/0192072 A1* | 6/2019 | Bailey | A61B 5/0002 |
| 2020/0008708 A1 | 1/2020 | Tan | |
| 2020/0357513 A1* | 11/2020 | Katra | G16H 40/63 |
| 2020/0410608 A1* | 12/2020 | Akutagawa | H04L 51/52 |
| 2021/0225505 A1* | 7/2021 | Khare | G06F 11/3089 |

OTHER PUBLICATIONS

"Swallowed capsule can identify health problems from inside the gut and send alert", News, May 30, 2018, 2 pps., <http://www.coloproctologynews.net/node/300>.

Johnson, "Swallowed electronic capsule could spot health trouble, send alert", Associated Press, The Chicago Tribune, May 25, 2018, <https://www.chicagotribune.com/lifestyles/health/ct-swallowed-electronic-capsule-20180525-story.html>.

Patent Cooperation Treaty PCT, International Searching Authority, Notification of Transmittal of the International Search Report and the Written Opinion of the International Searching Authority, or the Declaration, Date of mailing Dec. 14, 2021 (Dec. 14, 2021), Applicant's or agent's file reference PF210563PCT, International application No. PCT/CN2021/118793, International filing date Sep. 16, 2021 (Sep. 16, 2021), 9 pages.

Australian Government Examination Report, dated Jul. 22, 2024, regarding Application No. 2021348400, 2 pages.

\* cited by examiner

AUDIO-VISUAL INTERACTION WITH IMPLANTED DEVICES

BACKGROUND OF THE INVENTION

The present invention relates generally to the field of virtual assistants, and more particularly to audio-visual interaction with body implanted devices.

In recent years, developments in digital assistants and the growth of Internet of Things (IoT) capable devices have created competition to introduce new voice interfaces (e.g., for smart speakers, virtual assistance hardware/software, etc.) and functions. Cognitive analytics combines the use of cognitive computing and analytics. Cognitive computing combines artificial intelligence and machine-learning algorithms, in an approach that attempts to reproduce the behavior of the human brain. Analytics is the scientific process of transforming data into insights for making better decisions. Cognitive analytics applies intelligent technologies to bring unstructured data sources within reach of analytics processes for decision making and improved functions.

Augmented reality (AR) is an interactive experience of a real-world environment where the objects that reside in the real world are enhanced by computer-generated perceptual information, sometimes across multiple sensory modalities. AR can be defined as a system that fulfills three basic features: a combination of real and virtual worlds, real-time interaction, and accurate 3D registration of virtual and real objects. The overlaid sensory information can be constructive or destructive. The primary value of augmented reality is the manner in which components of the digital world blend into a person's perception of the real world, not as a simple display of data, but through the integration of immersive sensations, which are perceived as natural parts of an environment.

An implant is a medical device manufactured to replace, support, and/or enhance a biological structure. An active implantable medical device is any active medical device which is intended to be totally or partially introduced, surgically or medically, into the human body or by medical intervention into a natural orifice, and which is intended to remain after the procedure. Medical devices benefit patients by helping health care providers diagnose and treat patients and helping patients overcome sickness or disease, improving their quality of life.

SUMMARY

Aspects of the present invention disclose a method, computer program product, and system for audio-visual interaction of a user and implant device to resolve a voice command of the user. The method includes one or more processors determining a health-related issue of a user that corresponds to a voice command of the user. The method further includes one or more processors identifying an implanted device of the user that relates to the health-related issue. The method further includes one or more processors collecting sensor data of the implanted device, wherein the sensor data includes one or more conditions of the implanted device and operating environment of the implanted device in the body of the user. The method further includes one or more processors generating an audio-visual response corresponding to the health-related issue of the user based at least in part on the sensor data.

DETAILED DESCRIPTION

Embodiments of the present invention allow for audio-visual interactions of a user and implant device to resolve a voice command of the user. Embodiments of the present invention determine a condition of one or more implant devices of a user. Embodiments of the present invention enable a user to provide voice interaction with the one or more implant devices. Additional embodiments of the present invention generate recommended activities for a user based on endurance limitations of the user and/or parameters of the one or more implant devices. Further embodiments of the present invention generate audio-visual responses to a voice command of the user based on data feeds of the one or more implant devices.

Some embodiments of the present invention recognize that various implant devices are subject to influence by external electronic devices and implant failures. For example, implant failure refers to the failure of any medical implant to meet the claims of a manufacturer or a health care provider involved in installation. Implant failure can have any number of causes, such as mechanical degradation in the form of wear/fatigue, failures related to exposure to high voltage electricity or high intensity microwaves, or electrochemical degradation in the form of corrosion, can occur. However, the rates of failure vary for different implants. Embodiments of the present invention aid in preventing failures of implant devices by identifying the condition of implant devices and generating recommended activities within endurance limits of implant devices in real time.

Various embodiments of the present invention can operate to improve an implant device by utilizing data of sensors to determine whether the implant device is operating within defined performance parameters. Additionally, embodiments of the present invention can identify a root cause of underperformance. Furthermore, embodiments of the present invention enable voice interaction with an implant device utilizing Internet of Things (IoT) connectivity.

Implementation of embodiments of the invention may take a variety of forms, and exemplary implementation details are discussed subsequently with reference to the Figures.

Figure 1:
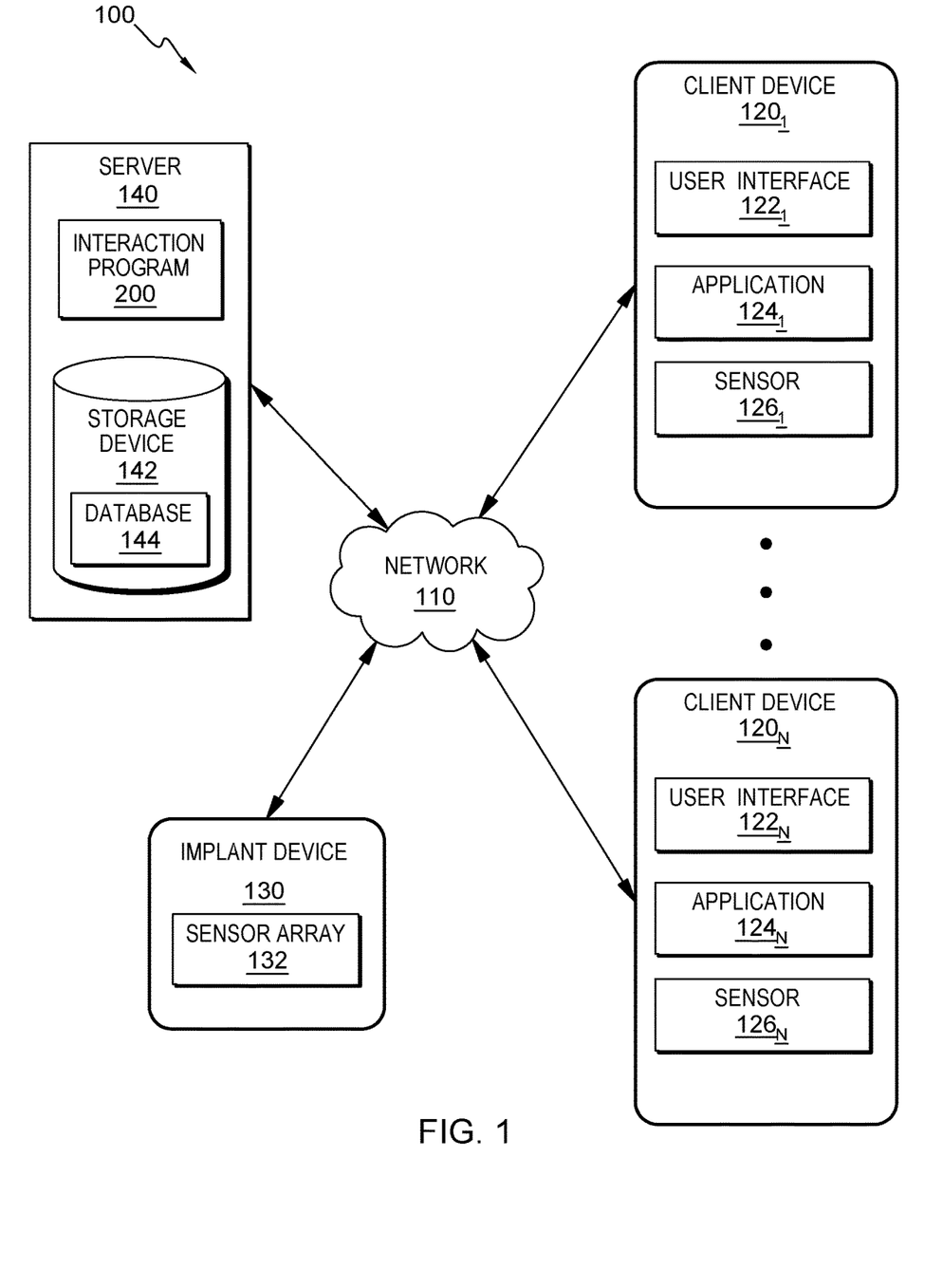
FIG. 1 is a functional block diagram of a data processing environment, in accordance with an embodiment of the present invention.

The present invention will now be described in detail with reference to the Figures. FIG. 1 is a functional block diagram illustrating a distributed data processing environment, generally designated 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

The present invention may contain various accessible data sources, such as database 144, implant device 130, or client device $120_{1-N}$, which may include personal data, content, or information the user wishes not to be processed. Personal data includes personally identifying information or sensitive personal information as well as user information, such as tracking or geolocation information. Processing refers to any, automated or unautomated, operation or set of operations such as collection, recording, organization, structuring, storage, adaptation, alteration, retrieval, consultation, use, disclosure by transmission, dissemination, or otherwise making available, combination, restriction, erasure, or destruction performed on personal data. Interaction program 200 enables the authorized and secure processing of personal data. Interaction program 200 provides informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. Interaction program 200 provides information regarding personal data and the nature (e.g., type, scope, purpose, duration, etc.) of the processing. Interaction program 200 provides the user with copies of stored personal data. Interaction program 200 allows the correction or completion of incorrect or incomplete personal data. Interaction program 200 allows the immediate deletion of personal data.

Distributed data processing environment 100 includes server 140, implant device 130, and client device 120$_{1-N}$, all interconnected over network 110. Network 110 can be, for example, a telecommunications network, a local area network (LAN) a municipal area network (MAN), a wide area network (WAN), such as the Internet, or a combination of the three, and can include wired, wireless, or fiber optic connections. Network 110 can include one or more wired and/or wireless networks capable of receiving and transmitting data, voice, and/or video signals, including multimedia signals that include voice, data, and video information. In general, network 110 can be any combination of connections and protocols that will support communications between server 140, implant device 130, and client device 120$_{1-N}$, and other computing devices (not shown) within distributed data processing environment 100.

Client device 120$_{1-N}$ (i.e., client device 120$_1$ through client device 120$_n$) can be one or more of a laptop computer, a tablet computer, a smart phone, smart watch, a smart speaker, virtual assistant, augmented reality (AR) glasses, Internet of Things (IoT) enabled device, or any programmable electronic device capable of communicating with various components and devices within distributed data processing environment 100, via network 110. In general, client device 120$_{1-N}$ represent one or more programmable electronic devices or combination of programmable electronic devices capable of executing machine readable program instructions and communicating with other computing devices (not shown) within distributed data processing environment 100 via a network, such as network 110. Client device 120$_{1-N}$ may include components as depicted and described in further detail with respect to FIG. 3, in accordance with embodiments of the present invention.

Client device 120$_{1-N}$ may include respective instances of user interface 122$_{1-N}$, application 124$_{1-N}$, and sensor 126$_{1-N}$, which each correspond to a respective instance of a client device and perform equivalent functions in the respective instance of the client device. In various embodiments of the present invention a user interface is a program that provides an interface between a user of a device and a plurality of applications that reside on the client device. A user interface, such as user interface 122$_1$, refers to the information (such as graphic, text, and sound) that a program presents to a user, and the control sequences the user employs to control the program. A variety of types of user interfaces exist. In one embodiment, user interface 122$_1$ is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In another embodiment, user interface 122$_1$ is a script or application programming interface (API). In one embodiment, user interface 122$_1$ is a voice user interface. A voice-user interface (VUI) makes spoken human interaction with computers possible, using speech recognition to understand spoken commands and answer questions, and typically text to speech to play a reply.

Application 124$_1$ is a computer program designed to run on client device 120$_1$. An application frequently serves to provide a user with similar services accessed on personal computers (e.g., web browser, playing music, e-mail program, or other media, etc.). In one embodiment, application 124$_1$ is mobile application software. For example, mobile application software, or an "app," is a computer program designed to run on smart phones, tablet computers and other mobile devices. In another embodiment, application 124$_1$ is a web user interface (WUI) and can display text, documents, web browser windows, user options, application interfaces, and instructions for operation, and include the information (such as graphic, text, and sound) that a program presents to a user and the control sequences the user employs to control the program. In another embodiment, application 124$_1$ is a client-side application of interaction program 200. For example, application 124$_1$ is an augmented reality application that combines virtual reality with the real world in the form of live video imagery that is digitally enhanced with computer-generated graphics.

Sensor 126$_1$ is a device, module, machine, or subsystem whose purpose is to detect events or changes in its environment and send the information to other electronics, frequently a computer processor. Generally, sensor 126$_1$ represents a variety of sensors of client device 120$_1$ that collects and provides various kinds of data (e.g., proximity, image, motion, electromagnetic field, radio frequency, light, etc.). In one embodiment, client device 120$_1$ transmits data of sensor 126$_1$ to server 140 via network 110. For example, sensor 126$_1$ can be a camera that client device 120$_1$ utilizes to capture images of an environment of a user, which are transmitted to a remote server (e.g., server 140).

In general, implant device 130 represent one or more programmable electronic devices or combination of programmable electronic devices capable of executing machine readable program instructions and communicating with other computing devices (not shown) within distributed data processing environment 100 via a network, such as network 110. Implant device 130 can include components as depicted and described in further detail with respect to FIG. 3, in accordance with embodiments of the present invention.

Implant device 130 is a medical device manufactured to replace a missing biological structure, support a damaged biological structure, enhance an existing biological structure, and/or localized medication/treatment delivery. Implant device 130 includes sensor array 132. In one embodiment, implant device 130 utilizes sensor array 132 to monitor functions of implant device 130 and/or an operating environment of implant device 130. For example, sensor 132 is one or more sensors of a medical device (e.g., joint replacement) implanted into a user. In this example, implant device 130 is paired via a WLAN (e.g., network 110) with a portable virtual assistant (e.g., client device $120_1$) to provide monitoring of a health status of a user and condition of implant device 130. Additionally, sensor array 132 can provide sensor feed data to the portable virtual assistant and a remote server (e.g., server 140).

In various embodiments of the present invention, server 140 may be a desktop computer, a computer server, or any other computer systems, known in the art. In general, server 140 is representative of any electronic device or combination of electronic devices capable of executing computer readable program instructions. Server 140 may include components as depicted and described in further detail with respect to FIG. 3, in accordance with embodiments of the present invention.

Server 140 can be a standalone computing device, a management server, a web server, a mobile computing device, or any other electronic device or computing system capable of receiving, sending, and processing data. In one embodiment, server 140 can represent a server computing system utilizing multiple computers as a server system, such as in a cloud computing environment. In another embodiment, server 140 can be a laptop computer, a tablet computer, a netbook computer, a personal computer (PC), a desktop computer, a personal digital assistant (PDA), a smart phone, or any programmable electronic device capable of communicating with client device $120_{1-N}$, implant device 130, and other computing devices (not shown) within distributed data processing environment 100 via network 110. In another embodiment, server 140 represents a computing system utilizing clustered computers and components (e.g., database server computers, application server computers, etc.) that act as a single pool of seamless resources when accessed within distributed data processing environment 100.

Server 140 includes storage device 142, database 144, and interaction program 200. Storage device 142 can be implemented with any type of storage device, for example, persistent storage 305, which is capable of storing data that may be accessed and utilized by client device $120_{1-N}$, implant device 130, and server 140, such as a database server, a hard disk drive, or a flash memory. In one embodiment storage device 142 can represent multiple storage devices within server 140. In various embodiments of the present invention, storage device 142 stores numerous types of data which may include database 144. Database 144 may represent one or more organized collections of data stored and accessed from server 140. For example, database 144 includes a knowledge corpus corresponding to a user, sensor feed data, medical records, implant device parameters, etc. In one embodiment, data processing environment 100 can include additional servers (not shown) that host additional information that accessible via network 110.

Generally, interaction program 200 communicates with wearable and IoT devices such as virtual assistants, which utilize sensor data of body implanted devices to determine a daily workload and health status of a user and recommend alternatives to reduce strain of the user. In one embodiment, interaction program 200 utilizes data of sensor array 132 to determine a condition of implant device 130 and a health status of a user. In another embodiment, interaction program 200 utilizes client device $120_{1-N}$ to enable user communication with one or more instances of implant device 130. In another embodiment, interaction program 200 utilizes client device $120_{1-N}$ to provide a user with visual display of current conditions of implant device 130. Also, interaction program 200 is capable of utilizing a live feed of an operating environment of client device $120_{1-N}$ to identify and recommend activities with respect to performance parameters of implant device 130 and/or health status of the user via an AR overlay.

Figure 2:
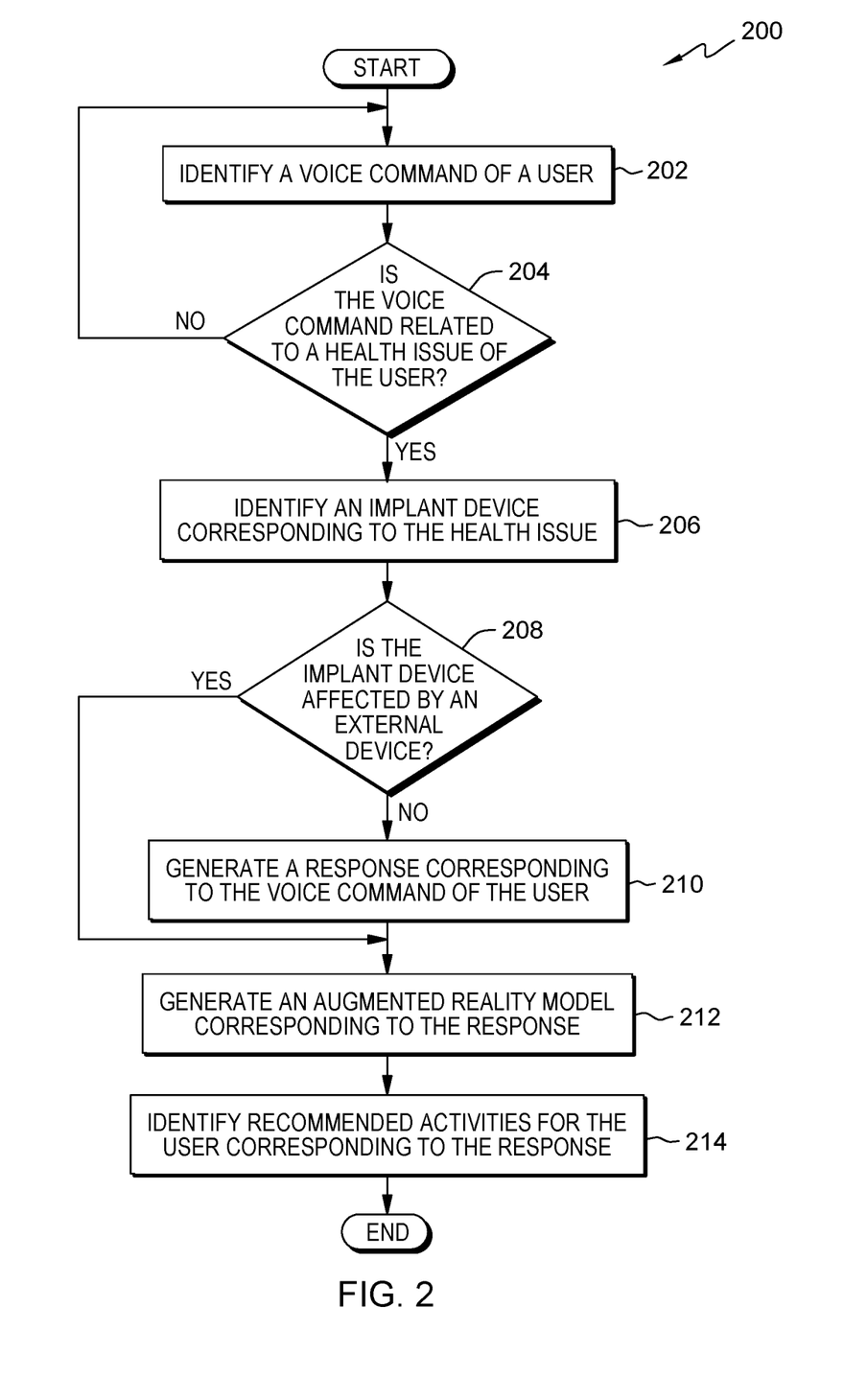
FIG. 2 is a flowchart depicting operational steps of a program for audio-visual interaction of a user and implant device to resolve a voice command of the user, in accordance with embodiments of the present invention.

FIG. 2 is a flowchart depicting operational steps of interaction program 200, a program for audio-visual interaction of a user and implant device to resolve a voice command of the user, in accordance with embodiments of the present invention. In one embodiment, interaction program 200 initiates in response to a user pairing implant device 130 with one instance of client device $120_{1-N}$ and interaction program 200 through network 110. For example, interaction program 200 initiates in response to a user registering (e.g., opting-in) a portable virtual assistant (e.g., client device $120_{1-N}$) with interaction program 200 via a WLAN (e.g., network 110). In another embodiment, interaction program 200 is a background application that continuously monitors client device $120_{1-N}$. For example, interaction program 200 is a client-side application (e.g., application $124_1$) that initiates upon booting of a portable virtual assistant (e.g., client device $120_{1-N}$) of a user and monitors the portable virtual assistant for a voice command.

In step 202, interaction program 200 identifies a voice command of a user. Various embodiments of the present invention enable a user to perform voice interaction with one or more implanted devices (e.g., implant device 130) of the user to determine a condition of the one or more implanted devices. For example, a portable AI voice assistant (e.g., client device $120_1$) is paired with implanted devices and/or IoT enabled sensors of the implanted devices of the user to allow the user to perform voice interaction with the implanted devices (i.e., based on the voice command, user can perform two-way voice interaction with one or more implanted devices). Additionally, allowing the user to ask specific question related to the one or more implanted devices or specify a problem the user is experiencing.

In one embodiment, interaction program 200 identifies a voice command of client device $120_1$ from a user. For example, interaction program 200 utilizes natural language processing (NLP) techniques (e.g., speech recognition, speech segmentation, tokenization, etc.) to identify a topic of a voice command of a user to a portable virtual assistant (e.g., client device $120_1$). In this example, interaction program 200 can utilize lexical semantics on a textual representation of audio of a user that includes a voice command the portable virtual assistant receives to identify the topic. In alternative example, interaction program 200 connects a portable virtual assistant (e.g., client device $120_1$) to an ingestible/injectable electronic device (e.g., implant device 130) to perform two-way voice interaction with the ingestible/injectable electronic device.

In another embodiment, interaction program 200 generates a knowledge corpus in storage device 142 corresponding to a user. For example, interaction program 200 collects historical data from various sources (e.g., sensors, medical records, etc.) to generate a knowledge corpus (e.g., database 144) that includes identified topics of voice commands, sensor feed data, health conditions, implant device parameters, etc. corresponding to a user. In this example, interaction program 200 connects (e.g., hosted on a cloud-based server) a portable virtual assistant (e.g., client device $120_1$) of the user to the knowledge corpus.

In decision step 204, interaction program 200 determines whether the voice command is related to a health issue of the user. In one embodiment, interaction program 200 utilizes data of database 144 corresponding to a user to determine whether a voice command of a user is related to a condition of implant device 130 and/or the user. For example, interaction program 200 utilizes a knowledge corpus (e.g., database 144) to determine whether a topic of a voice command of a user is related to one or more implanted medical devices (e.g., implant device 130) of a user. Also, interaction program 200 utilizes the knowledge corpus (e.g., database 144) to determine whether the topic of the voice command of the user is related to a health issue (e.g., health condition, medication delivery, pain, etc.) of the user. In this example, interaction program 200 utilizes NLP techniques (e.g., terminology extraction, lexical semantics, topic segmentation and recognition, etc.) to determine a relationship between the topic of the voice command and issues of the user.

In another embodiment, if interaction program 200 determines that a voice command of a user is not related to a condition of implant device 130 and/or the user (decision step 204, "NO" branch), then interaction program 200 continues to identify voice commands of client device $120_1$ from the user. In one scenario, if interaction program 200 determines that a topic of a voice command of a user is not related to an issue with the body, health, or status of one or more implanted medical devices (e.g., implant device 130) of the user, then interaction program 200 continues to identify topics of voice commands of the user to a portable virtual assistant (e.g., client device $120_1$).

In another embodiment, if interaction program 200 determines that a voice command of a user is related to a condition of implant device 130 and/or the user (decision step 204, "YES" branch), then interaction program 200 identifies an instance of implant device 130 related to the voice command of the user. In one scenario, if interaction program 200 determines that a topic of a voice command of a user is related to an issue with the body, health, or status of one or more implanted medical devices (e.g., implant device 130) of the user, then interaction program 200 utilizes a knowledge corpus (e.g., database 144) corresponding to the user to identify an implanted medical device of a user related to the issue.

In step 206, interaction program 200 identifies an implant device corresponding to the health issue. In various embodiments of the present invention, an implantable device can include various types sensors (e.g., temperature sensor, movement sensor, stress sensor etc.). The selection of the sensors can be based on the functions (e.g., orthopaedical, cardiovascular, etc.) of the implantable devices. For example, interaction program 200 correlates sensor feeds of wearable and implantable devices (e.g., implant device 130, client device $120_{1-N}$) and medical reports of a user to generate a knowledge corpus about health-related parameters and functions (e.g., implanted device malfunctions, associations of body parameters related to performance of the implanted devices, etc.).

In one embodiment, interaction program 200 utilizes database 144 to identify an instance of implant device 130 related to a voice command of a user. For example, interaction program 200 assigns one or more of the implanted medical devices (e.g., implant device 130) of a user a unique identifier (e.g., radio frequency identifier (RFID), series of values, etc.) and associates a location within the user with the unique identifier. In this example, interaction program 200 utilizes a topic (e.g., pain, function, health issue, implant status, etc.) of a voice command of the user and a knowledge corpus (e.g., database 144) to identify an implanted medical device (e.g., implant device 120) that corresponds to the topic of the voice command.

In decision step 208, interaction program 200 determines whether the implant device is affected by an external device. In various embodiments of the present invention each implanted device produces a sensor feed corresponding to mobility and activities of a user and performance of the implanted device. Additionally, interaction program 200 can utilize the sensor feed of normal functions of each implanted device to specify values for corresponding performance parameters of sensors.

In one embodiment, interaction program 200 determines whether client device 1202 affects performance of implant device 130. For example, interaction program 200 monitors one or more sensors (e.g., sensor array 132) of an implanted medical device (e.g., implant device 130) to identify a deviation from expected sensor values of performance parameters corresponding to sensor feeds of the implanted medical device. In this example, interaction program 200 determines whether the deviation is a result of the implanted medical device is receiving sensor feeds, which are influencing the performance of the medical implanted devices, from devices (e.g., IoT device, client device $120_2$, etc.) within an operating environment (e.g., body of user, immediate surroundings of user's body etc.) of the implanted medical device. In one scenario, interaction program 200 utilizes normal performance parameters of an electro-sensor (e.g., sensor array 132) of a pacemaker (e.g., implant device 130) to detect an external device (e.g., client device $120_2$) is emitting electromagnetic waves that are affecting the performance of the pacemaker. Additionally, interaction program 200 can identify one or more implanted medical devices of the user affecting the pacemaker.

In another embodiment, if interaction program 200 determines that client device $120_2$ affects performance of implant device 130 (decision step 208, "YES" branch), then interaction program 200 generates an AR object corresponding to implant device 130 and client device $120_2$. In one scenario, interaction program 200 determines that a deviation from expected sensor values of performance parameters corresponding to sensor feeds of an implanted medical device (e.g., implant device 130) result from devices (e.g., IoT device, client device $120_2$, etc.) within an operating environment (e.g., body of user, immediate surroundings of user's body etc.) of the implanted medical device. As a result, interaction program 200 generates a three-dimensional (3D) object, which represents the implanted medical device (e.g., implant device 130), in a virtual reality (VR) environment that displays indicators in a direction of the devices affecting the implanted medical device via wearable VR glasses (e.g., client device $120_3$).

In another embodiment, if interaction program 200 determines that client device $120_2$ does not affect performance of implant device 130 (decision step 208, "NO" branch), then interaction program 200 generates a response to a voice command from client device $120_1$ of a user. In one scenario, if interaction program 200 determines that a deviation from expected sensor values of performance parameters corresponding to sensor feeds of an implanted medical device (e.g., implant device 130) does not exist, then interaction program 200 generates an audio-visual response to the voice command of the user as discussed below in step 210.

In step 210, interaction program 200 generates a response corresponding to the voice command of the user. In one embodiment, interaction program 200 generates an audible response corresponding to a voice command of client device $120_1$ by a user. For example, interaction program 200 utilizes natural language generation (NLG) to convert information of a knowledge corpus (e.g., database 144) that corresponds to an implanted medical device (e.g., implant device 130), which was identified in step 206, to readable human language. In this example, interaction program 200 utilizes text-to-speech techniques to create an audio version of collected user data that is appropriate to convey identified causes of condition of a user or implanted medical device. Additionally, interaction program 200 uses a portable virtual assistant (e.g., client device $120_1$) to transmit the audible response corresponding to a voice command to the user.

In another example, interaction program 200 can identify a current state an implanted medical device (e.g., implant device 130) of a user based on collected data of a user (e.g., biometric data, sensor data, etc.). In this example, interaction program 200 utilizes endurance limits of the implanted medical device of a knowledge corpus (e.g., database 144) and sensor feed data (e.g., performance parameters) of the implanted device to determine whether the implanted device has exceeded a rated workload, performing within rated constraints, or ceased functioning properly (i.e., determine a current state based on deviation from normal performance parameters based on sensors such as stress, temperature, etc.). Additionally, interaction program 200 can utilize data (e.g., images, pressure readings, etc.) of one or more sensors (e.g., sensor array 132) of the implanted medical device to determine a condition of the body of the user in the location of the implanted medical device (e.g., determining a pain a person is feeling is due to inflammation around a knee replacement). In another example, interaction program 200 can determine a future state an implanted medical device (e.g., implant device 130) by estimating whether a current workload of the implanted medical device using performance parameters over a period of time would exceed an endurance limit of the user.

In step 212, interaction program 200 generates an augmented reality model corresponding to the response. In one embodiment, interaction program 200 utilizes data of sensor array 132 to generate an AR model of implant device 130 and an operating environment. Also, interaction program 200 utilizes client device $120_3$ to display the AR model to the user. For example, interaction program 200 can utilize images of an implantable medical device (e.g., implant device 130) to generate a 3D AR object corresponding to the implanted medical device. In this example, interaction program 200 utilizes images from a sensor feed (e.g., sensor array 132) of the implanted medical device to generate a visual representation of the health condition of an operating environment (e.g., area where implant is located in the body) of a user. Additionally, interaction program 200 can utilize sensor feeds from the implanted medical device to identify movement and performance information of the implanted medical device (i.e., allowing a real-time update of current condition and actions of implant device 130). Furthermore, interaction program 200 can utilize a pair of AR glasses (e.g., client device $120_3$) to display the 3D AR object and operating environment to user in response to a voice command of the user, which aids in convey generated response information to the user.

In another embodiment, interaction program 200 utilizes data of sensor $126_3$ of client device $120_3$ to generate a simulation model of an AR model of implant device 130. For example, interaction program 200 utilizes image data of a user from AR glasses (e.g., client device $120_3$) and IoT devices (e.g., client device $120_2$) to simulate performance of a 3D AR object corresponding to an implanted medical device (e.g., implant device 130). In one scenario, if interaction program 200 determines the implanted medical device is affected by an external device emitting electromagnetic waves, then interaction program 200 can utilize image data of the AR glasses to display an indication of a direction of the external device (e.g., client device $120_2$).

In step 214, interaction program 200 identifies recommended activities for the user corresponding to the response. In one embodiment, interaction program 200 utilizes data of sensor $126_3$ of client device $120_3$ to determine activities for a user to perform based on implant device 130. For example, interaction program 200 utilizes a camera feed of AR glasses (e.g., client device $120_3$) and object recognition to identify activities that create an adverse effect on an implanted medical device (e.g., implant device 130) based on a current condition of the implanted device or health status of a user. In this example, interaction program 200 utilizes an overlay to identify (e.g., highlight, bound, etc.) objects in an area surrounding the user that may cause the user to exceed an endurance limit of the implanted medical device. Additionally, interaction program 200 utilizes the AR glasses to display recommended activities and prohibited activities in real-time.

In one scenario, interaction program 200 identifies a skateboard, stairs, and an elevator (e.g., objects) in an area surrounding a user. Additionally, interaction program 200 determines that the user has an implanted knee (e.g., implant device 130) with swelling (e.g., current health condition of the user). As a result, interaction program 200 transmits visual recommendation to the user via AR glasses (e.g., client device $120_3$) by inputting images into an overlay corresponding to each object in the feed of the AR glasses that indicate approval or prohibition of an activity related to the object. Accordingly, interaction program 200 approves of the user utilizing an elevator and prohibits use of the stairs and skateboard based on the capability of the implanted knee (e.g., implant not rated for stress caused by skateboarding) and user condition (e.g., swelling of the knee).

Figure 3:
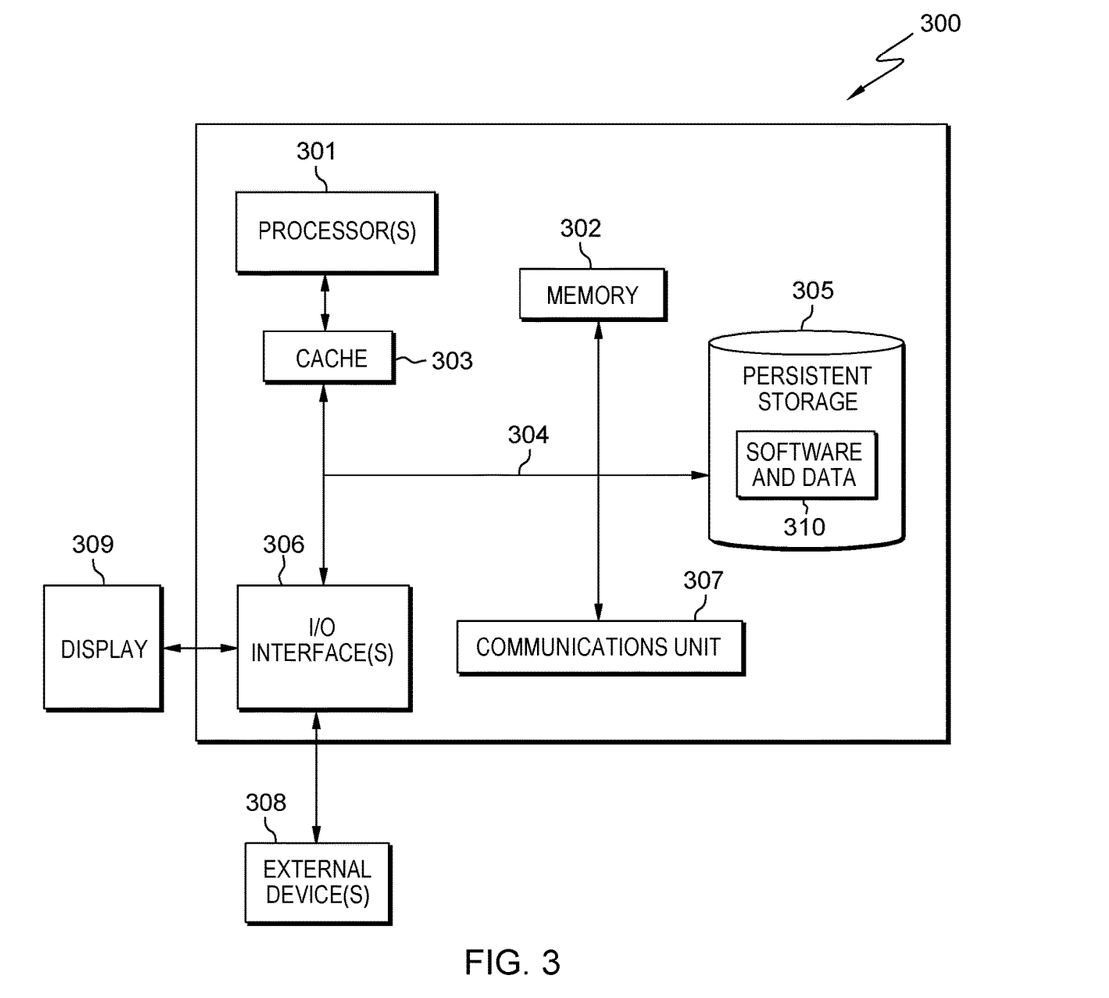
FIG. 3 is a block diagram of components of FIG. 1, in accordance with an embodiment of the present invention.

FIG. 3 depicts a block diagram of components of client device $120_{1-N}$, implant device 130 and server 140, in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

FIG. 3 includes processor(s) 301, cache 303, memory 302, persistent storage 305, communications unit 307, input/output (I/O) interface(s) 306, and communications fabric 304. Communications fabric 304 provides communications between cache 303, memory 302, persistent storage 305, communications unit 307, and input/output (I/O) interface(s) 306. Communications fabric 304 can be implemented with any architecture designed for passing data and/or control information between processors (such as microprocessors, communications and network processors, etc.), system memory, peripheral devices, and any other hardware components within a system. For example, communications fabric 304 can be implemented with one or more buses or a crossbar switch.

Memory 302 and persistent storage 305 are computer readable storage media. In this embodiment, memory 302 includes random access memory (RAM). In general, memory 302 can include any suitable volatile or non-volatile computer readable storage media. Cache 303 is a fast memory that enhances the performance of processor(s) 301 by holding recently accessed data, and data near recently accessed data, from memory 302.

Program instructions and data (e.g., software and data 310) used to practice embodiments of the present invention may be stored in persistent storage 305 and in memory 302 for execution by one or more of the respective processor(s) 301 via cache 303. In an embodiment, persistent storage 305 includes a magnetic hard disk drive. Alternatively, or in addition to a magnetic hard disk drive, persistent storage 305 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 305 may also be removable. For example, a removable hard drive may be used for persistent storage 305. Other examples include optical and magnetic disks, thumb drives, and smart cards that are inserted into a drive for transfer onto another computer readable storage medium that is also part of persistent storage 305. Software and data 310 can be stored in persistent storage 305 for access and/or execution by one or more of the respective processor(s) 301 via cache 303. With respect to client device $120_{1-N}$, software and data 310 includes data of user interface $122_{1-N}$, application $124_{1-N}$, sensor and $126_{1-N}$. With respect to implant device 130, software and data 310 includes data of user sensor array 132. With respect to server 140, software and data 310 includes data of storage device 142 and interaction program 200.

Communications unit 307, in these examples, provides for communications with other data processing systems or devices. In these examples, communications unit 307 includes one or more network interface cards. Communications unit 307 may provide communications through the use of either or both physical and wireless communications links. Program instructions and data (e.g., software and data 310) used to practice embodiments of the present invention may be downloaded to persistent storage 305 through communications unit 307.

I/O interface(s) 306 allows for input and output of data with other devices that may be connected to each computer system. For example, I/O interface(s) 306 may provide a connection to external device(s) 308, such as a keyboard, a keypad, a touch screen, and/or some other suitable input device. External device(s) 308 can also include portable computer readable storage media, such as, for example, thumb drives, portable optical or magnetic disks, and memory cards. Program instructions and data (e.g., software and data 310) used to practice embodiments of the present invention can be stored on such portable computer readable storage media and can be loaded onto persistent storage 305 via I/O interface(s) 306. I/O interface(s) 306 also connect to display 309.

Display 309 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an electromagnetic storage device, an optical storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for audio-visual interaction with implanted devices, the method comprising:
   determining, by one or more processors, a health-related issue of a user based, at least in part, on historical medical data corresponding to the user and a voice command of the user;
   identifying, by the one or more processors, an implanted device of the user that relates to the health-related issue of the user that was determined based at least in part on the historical medical data corresponding to the user and the voice command of the user;
   collecting, by the one or more processors, sensor data of the implanted device, wherein the sensor data includes one or more conditions of the implanted device and operating environment of the implanted device in the body of the user; and
   generating, by the one or more processors, an audio-visual response corresponding to the health-related issue of the user based at least in part on the sensor data that includes the one or more conditions of the implanted device and operating environment of the implanted device in the body of the user.

2. The method of claim 1, further comprising:
   generating, by the one or more processors, a three-dimensional augmented reality (AR) object corresponding to the implanted device based at least in part on the collected sensor data; and
   generating, by the one or more processors, a visual representation of a condition of the operating environment of the implanted device in the body of the user based at least in part on the collected sensor data that includes the one or more conditions of the implanted device and operating environment of the implanted device in the body of the user.

3. The method of claim 1, further comprising:
   identifying, by the one or more processors, one or more objects within a sensor feed of an AR device;
   determining, by the one or more processors, whether an activity associated with the one or more objects adversely affects the user based at least in part on the one or more conditions of the implanted device and the operating environment of the implanted device; and
   generating, by the one or more processors, an overlay corresponding to each of the one or more objects, wherein the overlay indicates a recommendation of approval of one or more activities associated with the one or more objects.

4. The method of claim 1, further comprising:
   determining, by the one or more processors, whether a second device affects performance of the implanted device, wherein the second device is selected from a group consisting of: a second implanted device and external device.

5. The method of claim 1, wherein identifying the implanted device of the user that relates to the health-related issue, further comprises:
   correlating, by the one or more processors, one or more topics of the voice command with one or more conditions of the health-related issue of the user that was determined based at least in part on the historical medical data corresponding to the user and the voice command of the user; and
   identifying, by the one or more processors, one or more implanted devices with a performance function that relates to the one or more topics of the voice command.

6. The method of claim 1, wherein generating the audio-visual response corresponding to the health-related issue of the user, further comprises:
- determining, by the one or more processors, a state of the implanted device based on the collected sensor data of the implanted device that relates to the voice command of the user;
- determining, by the one or more processors, a condition of the body of the user in the location of the implanted device; and
- generating, by the one or more processors, an audible response that includes information corresponding to the voice command of the user, wherein the information is based at least in part on the state of the implanted device and the condition of the body of the user in the location of the implanted device.

7. The method of claim 6, further comprising:
- transmitting, by the one or more processors, a three-dimensional augmented reality object corresponding to the implanted device and the audible response to the user through one or more computing devices, wherein at least one of the one or more computing devices includes an augmented reality enabled device.

8. A computer program product for audio-visual interaction with implanted devices, the computer product comprising:
- one or more computer readable storage media and program instructions stored on the one or more computer readable storage media, the program instructions comprising:
- program instructions to determine a health-related issue of a user based, at least in part, on historical medical data corresponding to the user and a voice command of the user;
- program instructions to identify an implanted device of the user that relates to the health-related issue of the user that was determined based at least in part on the historical medical data corresponding to the user and the voice command of the user;
- program instructions to collect sensor data of the implanted device, wherein the sensor data includes one or more conditions of the implanted device and operating environment of the implanted device in the body of the user; and
- program instructions to generate an audio-visual response corresponding to the health-related issue of the user based at least in part on the sensor data that includes the one or more conditions of the implanted device and operating environment of the implanted device in the body of the user.

9. The computer program product of claim 8, further comprising program instructions, stored on the one or more computer readable storage media, to:
- generate a three-dimensional augmented reality (AR) object corresponding to the implanted device based at least in part on the collected sensor data; and
- generate a visual representation of a condition of the operating environment of the implanted device in the body of the user based at least in part on the collected sensor data that includes the one or more conditions of the implanted device and operating environment of the implanted device in the body of the user.

10. The computer program product of claim 8, further comprising program instructions, stored on the one or more computer readable storage media, to:
- identify one or more objects within a sensor feed of an AR device;
- determine whether an activity associated with the one or more objects adversely affects the user based at least in part on the one or more conditions of the implanted device and the operating environment of the implanted device; and
- generate an overlay corresponding to each of the one or more objects, wherein the overlay indicates a recommendation of approval of one or more activities associated with the one or more objects.

11. The computer program product of claim 8, further comprising program instructions, stored on the one or more computer readable storage media, to:
- determine whether a second device affects performance of the implanted device, wherein the second device is selected from a group consisting of: a second implanted device and external device.

12. The computer program product of claim 8, wherein program instructions to identify the implanted device of the user that relates to the health-related issue, further comprise program instructions to:
- correlate one or more topics of the voice command with one or more conditions of the health-related issue of the user that was determined based at least in part on the historical medical data corresponding to the user and the voice command of the user; and
- identify one or more implanted devices with a performance function that relates to the one or more topics of the voice command.

13. The computer program product of claim 8, wherein program instructions to generate the audio-visual response corresponding to the health-related issue of the user, further comprise program instructions to:
- determine a state of the implanted device based on the collected sensor data of the implanted device that relates to the voice command of the user;
- determine a condition of the body of the user in the location of the implanted device; and
- generate an audible response that includes information corresponding to the voice command of the user, wherein the information is based at least in part on the state of the implanted device and the condition of the body of the user in the location of the implanted device.

14. The computer program product of claim 13, further comprising program instructions, stored on the one or more computer readable storage media, to:
- transmit a three-dimensional augmented reality object corresponding to the implanted device and the audible response to the user through one or more computing devices, wherein at least one of the one or more computing devices includes an augmented reality enabled device.

15. A computer system for audio-visual interaction with implanted devices, the computer system comprising:
- one or more computer processors;
- one or more computer readable storage media; and
- program instructions stored on the computer readable storage media for execution by at least one of the one or more processors, the program instructions comprising:
- program instructions to determine a health-related issue of a user based, at least in part, on historical medical data corresponding to the user and a voice command of the user;
- program instructions to identify an implanted device of the user that relates to the health-related issue of the user that was determined based at least in part on the historical medical data corresponding to the user and the voice command of the user;

program instructions to collect sensor data of the implanted device, wherein the sensor data includes one or more conditions of the implanted device and operating environment of the implanted device in the body of the user; and program instructions to generate an audio-visual response corresponding to the health-related issue of the user based at least in part on the sensor data that includes the one or more conditions of the implanted device and operating environment of the implanted device in the body of the user.

16. The computer system of claim 15, further comprising program instructions, stored on the one or more computer readable storage media for execution by at least one of the one or more processors, to:

generate a three-dimensional augmented reality (AR) object corresponding to the implanted device based at least in part on the collected sensor data; and generate a visual representation of a condition of the operating environment of the implanted device in the body of the user based at least in part on the collected sensor data that includes the one or more conditions of the implanted device and operating environment of the implanted device in the body of the user.

17. The computer system of claim 15, further comprising program instructions, stored on the one or more computer readable storage media for execution by at least one of the one or more processors, to:

identify one or more objects within a sensor feed of an AR device;

determine whether an activity associated with the one or more objects adversely affects the user based at least in part on the one or more conditions of the implanted device and the operating environment of the implanted device; and generate an overlay corresponding to each of the one or more objects, wherein the overlay indicates a recommendation of approval of one or more activities associated with the one or more objects.

18. The computer system of claim 15, further comprising program instructions, stored on the one or more computer readable storage media for execution by at least one of the one or more processors, to:

determine whether a second device affects performance of the implanted device, wherein the second device is selected from a group consisting of: a second implanted device and external device.

19. The computer system of claim 15, wherein identify the implanted device of the user that relates to the health-related issue, further comprise program instructions to:

correlate one or more topics of the voice command with one or more conditions of the health-related issue of the user that was determined based at least in part on the historical medical data corresponding to the user and the voice command of the user; and identify one or more implanted devices with a performance function that relates to the one or more topics of the voice command.

20. The computer system of claim 15, wherein generate the audio-visual response corresponding to the health-related issue of the user, further comprise program instructions to:

determine a state of the implanted device based on the collected sensor data of the implanted device that relates to the voice command of the user;

determine a condition of the body of the user in the location of the implanted device; and generate an audible response that includes information corresponding to the voice command of the user, wherein the information is based at least in part on the state of the implanted device and the condition of the body of the user in the location of the implanted device.

* * * * *